US00PP23433P3

(12) United States Plant Patent
Deng et al.

(10) Patent No.: US PP23,433 P3
(45) Date of Patent: Feb. 26, 2013

(54) ***GERBERA* PLANT NAMED 'UFGE 7034'**

(50) Latin Name: *Gerbera hybrida*
Varietal Denomination: UFGE 7034

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 32 days.

(21) Appl. No.: 13/068,288

(22) Filed: May 5, 2011

(65) Prior Publication Data

US 2012/0284891 P1 Nov. 8, 2012

(51) Int. Cl.
*A01H 5/00* (2006.01)

(52) U.S. Cl. ..... Plt./357

(58) Field of Classification Search ..... Plt./357
See application file for complete search history.

*Primary Examiner* — Susan McCormick Ewoldt

(57) ABSTRACT

A new *Gerbera* plant particularly distinguished by having a novel combination of early flowering, medium lengths of peduncles, double orange-red inflorescence, an overall inflorescence diameter of approximately 11 cm, high inflorescence counts, a moderate level of resistance to powdery mildew, and demonstrated potential to produce attractive plants in large (≧20-cm in diameter) containers, is disclosed.

3 Drawing Sheets

Genus and species: *Gerbera hybrida.*
Variety denomination: 'UFGE 7034'.

BACKGROUND OF THE NEW PLANT

The invention relates to a new and distinct variety of *Gerbera hybrida* plant named 'UFGE 7034'. 'UFGE 7034' originated from a cross made at Wimauma, Fla. in 2005 between the female parent, 'UFGE 5006' (unpatented), an unreleased breeding line selected at Bradenton, Fla. from a population of progeny of the cross 'UFGE 39-26' (unpatented) and 'UFGE 5-23' (unpatented), and the male parent, 'Sunburst Yellow' (unpatented). 'UFGE 7034' was selected by the inventors from the progeny of the stated parentage in summer 2007 at Wimauma, Fla. The first asexual reproduction of 'UFGE 7034' was accomplished when crown division was done in late 2007 at Wimauma, Fla. Plants of 'UFGE 7034' have been asexually propagated by crown division and/or tissue culture for more than three generations. Asexually propagated plants of 'UFGE 7034' have remained true to the original selected plant, and all characteristics of the plant have been transmitted and retained through three successive asexual vegetative generations.

Plant Breeder's Rights for this cultivar have not been applied for. 'UFGE 7034' has not been made publicly available more than one year prior to the filing of this application.

SUMMARY OF THE INVENTION

The new and distinct variety of *Gerbera* plant is characterized by a novel combination of early flowering, medium lengths of peduncles, double orange-red inflorescences, an overall inflorescence diameter of approximately 11 cm, high inflorescence counts, a moderate level of resistance to powdery mildew, and demonstrated potential to produce attractive plants in large (≧20-cm in diameter) containers. 'UFGE 7034' has not been observed under all possible environmental conditions. Its phenotype may vary significantly with variations in environment such as light intensity, temperature, and day length. The following are the most outstanding and distinguishing characteristics of this new cultivar when grown at Wimauma, Fla. under normal horticultural practices in greenhouse conditions which closely approximate those generally used in commercial practice.

1. Peduncle length of approximately 38 cm;
2. Double inflorescence type;
3. Orange-red (RHS 30C) ray florets;
4. Yellow-green (RHS 151D) discs before opening of disc florets;
5. Yellow (RHS 13C) perianth lobe of disc florets;
6. Inflorescence diameter of approximately 11 cm;
7. High inflorescence count;
8. Moderate resistance to powdery mildew; and
9. Early flowering.

DESCRIPTION OF THE PHOTOGRAPHS

This new *Gerbera* plant is illustrated by the accompanying photographs which show the plant's form, inflorescences, and foliage. The colors shown are as true as can be reasonably obtained by conventional photographic procedures. The photographs are of a plant approximately 2 months old which was produced from one tissue culture liner and is potted in a 2.7-L container. Colors in the photograph may differ slightly from the color values cited in the detailed botanical description, which accurately describe the colors of the new *Gerbera.*

DESCRIPTION OF THE NEW CULTIVAR

Figure 1:
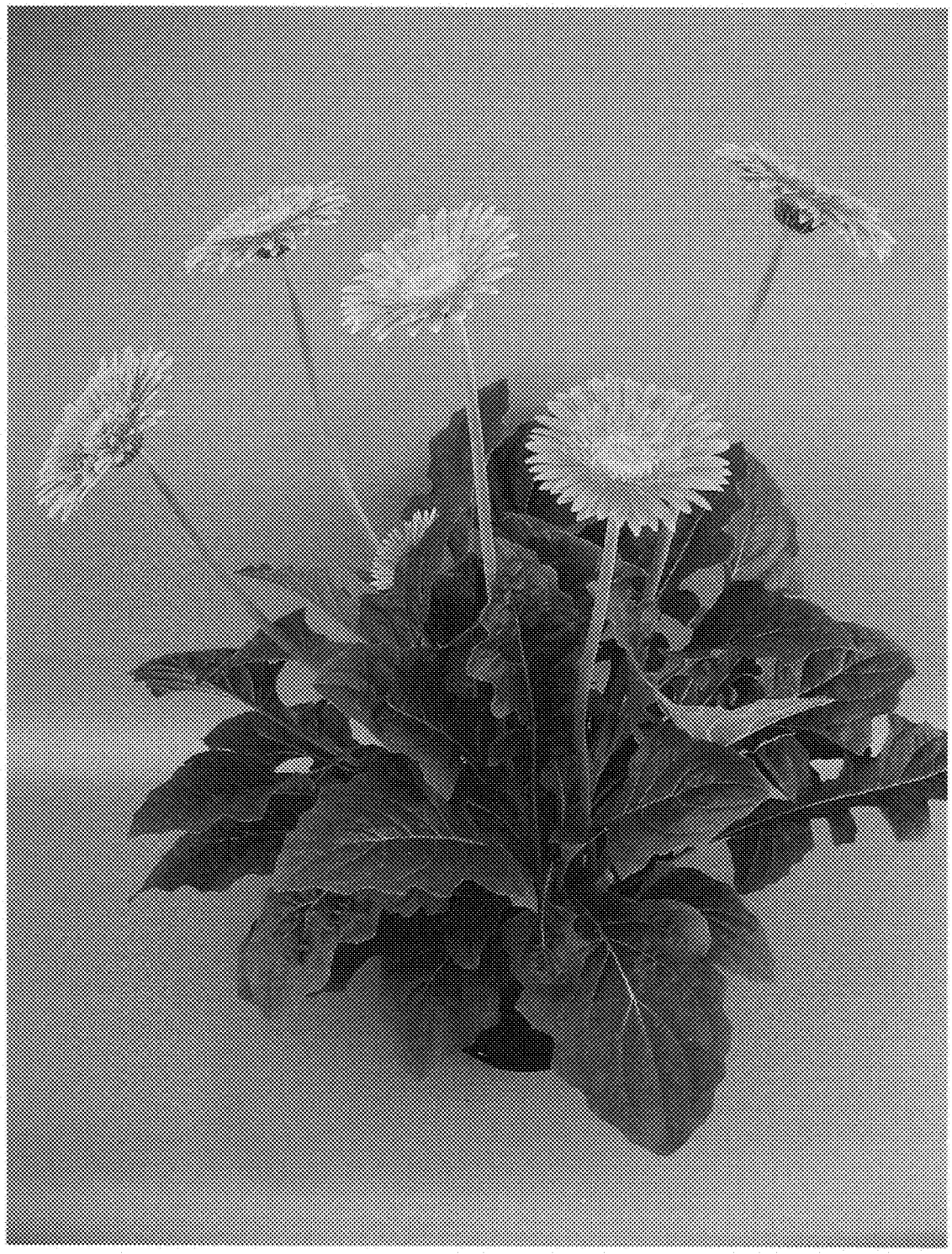
FIG. 1 shows the overall plant habit including inflorescences and foliage and is taken from a side perspective view.
Figure 2:
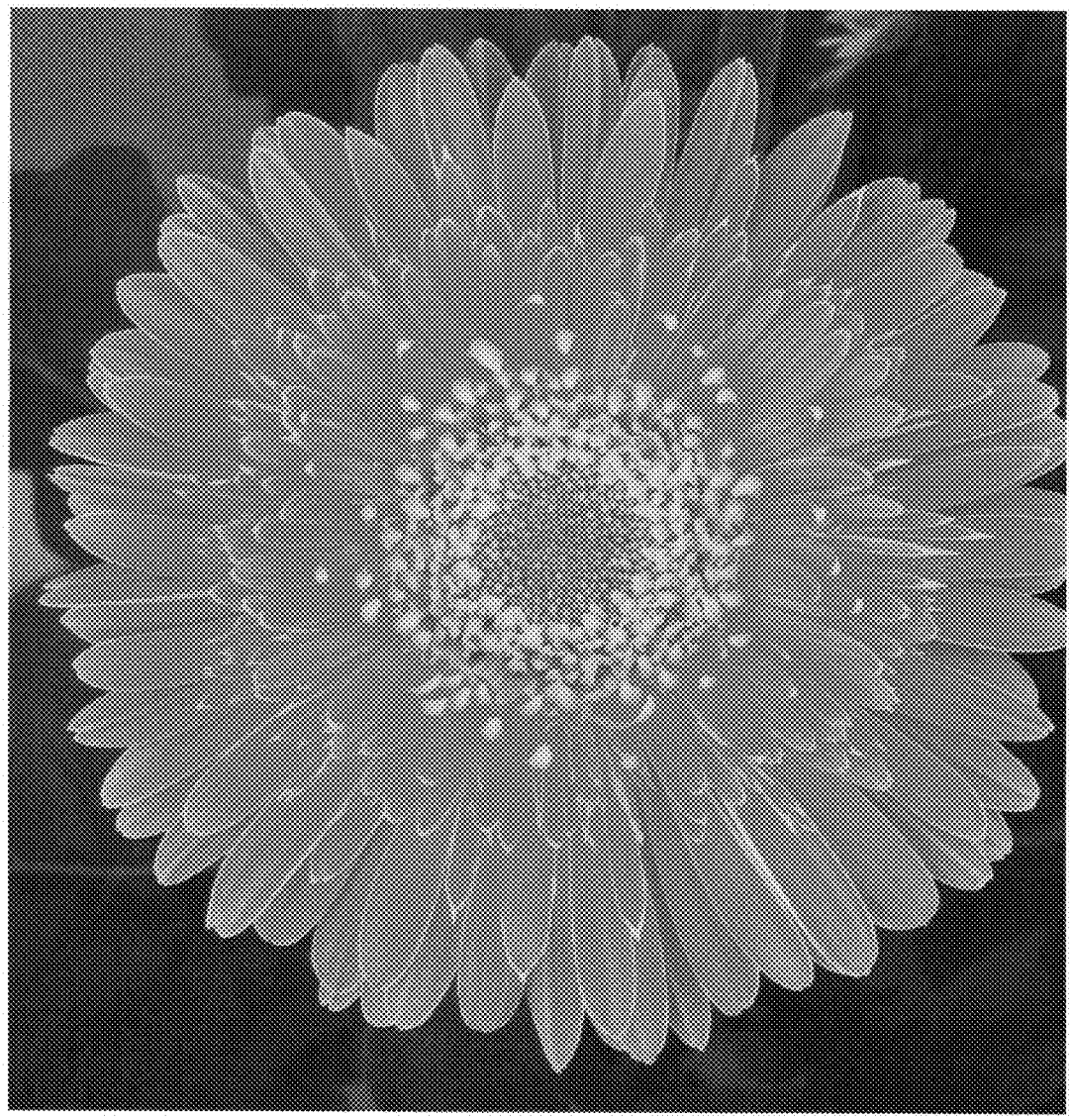
FIG. 2 shows a close-up of the inflorescence.
Figure 3:
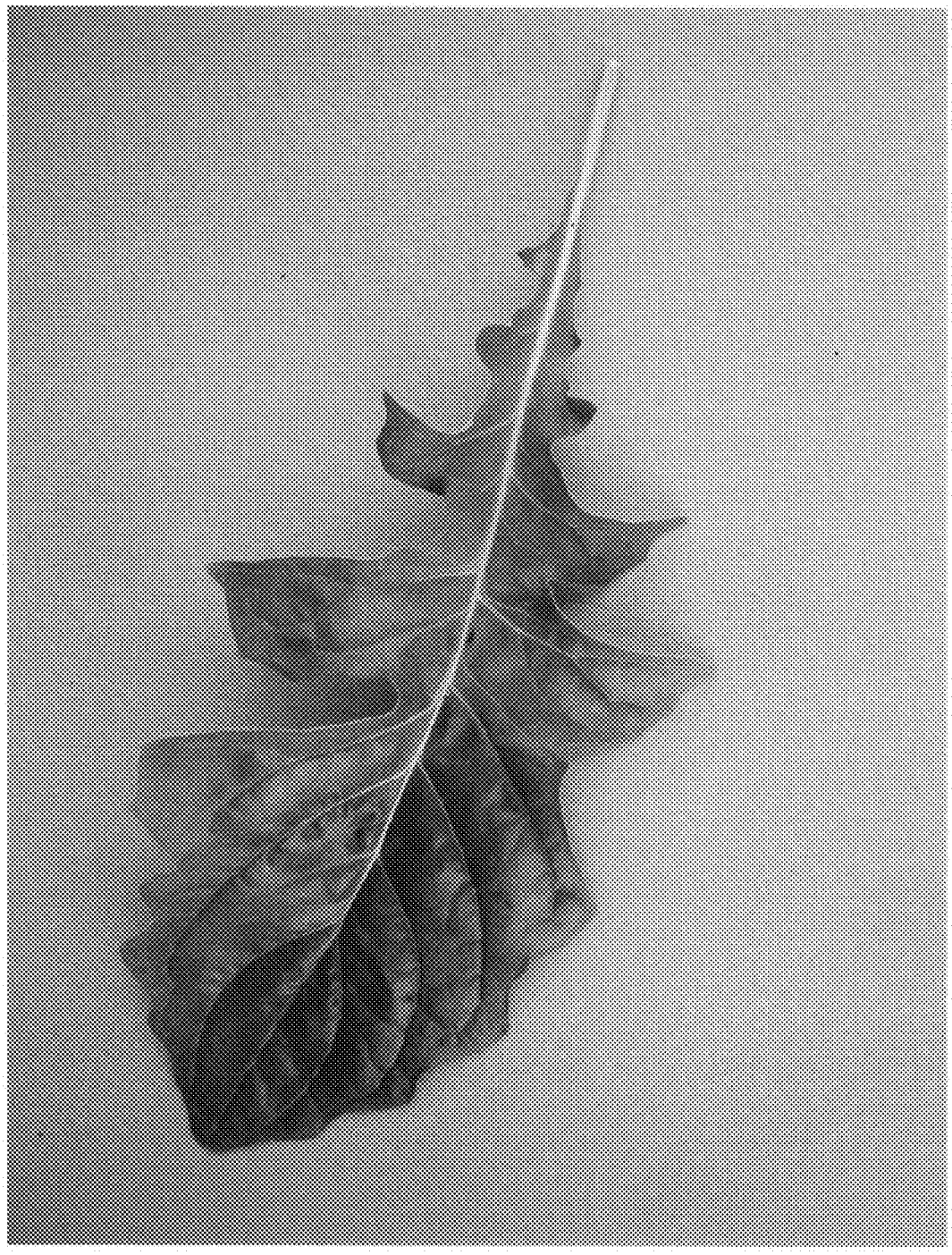
FIG. 3 shows a close-up of the typical leaf.

The following detailed description sets forth the distinctive characteristics of 'UFGE 7034'. The present botanical description is that of the variety at approximately 2 months old on Oct. 21, 2009 at 3:30 p.m. in a room under north light at Wimauma, Fla. The colors (except those in common terms)

are described from R.H.S. Colour Chart published by The Royal Horticultural Society in London (1986 ed.), in association with the Flower Council of Holland.

DETAILED BOTANICAL DESCRIPTION

Classification:

*Botanical.*—*Gerbera hybrida* cv. 'UFGE 7034'.

*Common name.*—*Gerbera.*

Parentage:

*Female, or seed, parent.*—'UFGE 5006' (unpatented).

*Male, or pollen, parent.*—'Sunburst Yellow' (unpatented).

Inflorescence:

*Appearance.*—Double type inflorescence form; solitary inflorescences borne on upright and strong scapes above the foliar plane; ray and disc florets arranged acropetally on a capitulum.

*Color* (*general tonality from a distance of* 3 *meters*).—Orange-red (RHS 30C).

*Shape.*—Moderately incurving funnel-shaped.

*Fragrance.*—None detected.

*Flowering season.*—Plants begin flowering about six weeks after planting and flower year-round in outdoor gardens in Wimauma, Fla., until plants are killed by frosts or freezes; plants flower year-round under greenhouse conditions in Wimauma, Fla.

*Inflorescence longevity.*—Inflorescences last about two to three weeks on the plant in Wimauma, Fla.; inflorescences not persistent.

*Quantity of inflorescences.*—Free flowering habit, with up to 20 open and developing inflorescences per plant at one time.

*Inflorescence bud.*—Height: About 1.2 cm. Diameter: About 2 cm. Shape: Oblate. Color (opening buds): Close to yellow-green (RHS 151D).

*Inflorescence size.*—Diameter: About 11 cm. Depth (height): About 1.9 cm. Diameter of disc: About 3.1 cm. Receptacle height: About 3 mm. Receptacle diameter: About 2 cm. Receptacle color: Close to green-white (RHS 157A).

*Phyllaries.*—Number of phyllaries per inflorescence: About 86 arranged in about three whorls. Length: About 1.3 cm. Width: About 3 mm. Shape: Subulate. Apex: Narrowly acute. Base: Truncate. Margin: Entire. Texture, upper surface: Smooth, glabrous. Texture, lower surface: Moderately tomentose. Color, upper surface: Close to green (RHS 144A). Color, lower surface: Close to green (RHS 137C). Color, towards the base: Close to green (RHS 137B). Longitudinal axis of inner rows: Straight. Anthocyanin: Absent.

*Inner ray florets.*—Number per inflorescence: About 142 arranged in about four whorls. Length: About 3.7 cm. Width: About 3 mm. Shape: Narrow elliptic. Apex: Emarginate to obtuse. Base: Truncate. Margin: Entire. Texture, upper surface: Smooth, glabrous, slightly velvety, longitudinally ridged. Texture, lower surface: Smooth, glabrous, slightly velvety, longitudinally ridged. Color, upper surface: Close to orange-red (RHS 30C and 30D). Color, lower surface: Close to yellow (RHS 8A and 8B). Longitudinal axis of outer row: Moderately reflexing. Longitudinal axis of inner rows: Straight.

*Outer ray floret.*—Number: About 58 arranged in three whorls. Cross section: Concave. Length: Medium, approx. 41 mm. Width: Medium, approx 6 mm. Shape: Narrow elliptic. Apex: Emarginate to obtuse. Base: Truncate. Margin: Entire. Depth of incision: None to very shallow. Texture, upper surface: Smooth, glabrous, slightly velvety, longitudinally ridged. Texture, lower surface: Smooth, glabrous, slightly velvety, longitudinally ridged. Color (topside): Close to orange-red (RHS 30C). Color (bottom side): Close to yellow-orange (RHS 23C). Color distribution on inner side: Uniform. Edge of different color: Absent.

*Disc florets.*—Number: About 325. Length: About 1.9 cm. Width: About 3 mm. Shape: Tubular, fused. Apex: Narrowly obtuse. Base: Fused. Margin: Entire. Texture, upper and lower surfaces: Smooth, glabrous. Color, fully opened upper surface: Close to yellow (RHS 13C). Color, fully opened lower surface: Close to yellow (RHS 13C). Disc diameter: Medium, approx. 31 mm.

*Reproductive organs.*—Androecium: On most disc florets; quantity: one. Gynoecium: On ray and disc florets; quantity per floret: one. Filament length: About 4 mm. Filament color: Close to white (155B). Anther shape: Linear. Anther length: About 3 mm. Anther width: About 1 mm. Style color: Close to yellow (RHS 8B). Stigma color: Close to yellow (RHS 8C). Anther color: Close to yellow (RHS 13B). Pollen, amount: Extremely scarce, highly sterile. Pollen color: Not possible to determine due to lack of pollen. Pistil per floret: One. Pistil length: About 1.6 cm. Stigma shape: Cleft. Style length: About 1.2 cm. Ovary color: Close to white (RHS 155A).

*Pappus.*—Quantity of hairs per floret: About 91. Length: About 6 mm. Diameter: Less than 1 mm. Texture: Soft. Main color: Close to yellow-white (RHS 158D).

*Peduncle.*—Length: Medium, approx. 38 cm. Tendency to fasciation: Absent. Thickness: Medium, approx. 7 mm. Strength: Strong. Texture: Moderately densely tomentose. Color: Close to yellow-green (RHS 144B). Anthocyanin coloration: At base: greyed purple (RHS 182A). At top: Absent.

Plant:

*General appearance.*—Herbaceous perennial, typically grown as container or garden plants; upright and mounding growth habit, roughly globular in shape; leaves arranged in basal rosettes and outwardly arching; dense and bushy habit; inflorescences held above the foliar plane on erect and strong basal peduncles (or scapes); moderately vigorous.

*Plant height, soil level to top of foliar plane.*—Approx. 30 cm.

*Plant height, soil level to top of inflorescence.*—About 40 cm.

*Plant width.*—Approx. 60 cm.

*Foliage.*—Leaf arrangement: Basal rosette, alternate, simple. Leaf blade: Length: Approx. 26 cm. Width: Approx. 13 cm. Shape: Oblong. Blistering: Weak. Depth of incisions in leaf: Basal part: Deep. Central part: Medium. Distal part: Shallow. Base: Truncate. Margin: Irregular crenate, sinuses divergent, undulate. Texture, upper surface: Sparsely pubescent. Texture, lower surface: Moderately pubescent. Venation pattern: Pinnate. Color: Upper side: Yellow-green (RHS 137A). Bottom side: Yellow-green (RHS 147B). Glossiness on upper side: Medium. Apex: Obtuse.

*Petiole*.—Petiole length: Approx. 8 cm. Diameter: About 4 mm. Texture, upper and lower surfaces: Moderately pubescent. Color, upper and lower surfaces: Close to yellow-green (RHS 144B). Color, proximal end: Close to greyed-purple (RHS 182C). Petiole anthocyanin coloration: Weak (red-purple, RHS 60B and 60C).

Resistance to diseases: 'UFGE 7034' has been observed in multiple experiments in which it was compared with two common commercial cultivars, 'Pensacola' *gerbera* (unpatented) and 'Bimini' *gerbera* (unpatented), for the incidence and severity of powdery mildew, *Podosphaera* (syn. *Sphaerotheca*) *fusca* (Fr.) S. Blumer. 'UFGE 7034' has consistently been found to have a moderate level of resistance to powdery mildew. In two experiments conducted, Experiment 1 in winter 2008 and spring 2009, and Experiment 2 in summer and fall 2009, both at Wimauma, Fla., tissue culture liners of 'UFGE 7034', 'Bimini', and 'Pensacola' were transplanted into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Plants were grown under a plastic tunnel within a screen house with approximately 45% light exclusion. Fungicides were not applied throughout the experiments to subject the plants to natural powdery mildew disease pressures. In Experiment 1, the severity of powdery mildew on *gerbera* leaves was assessed at week 8 after transplanting (Feb. 4, 2009), week 10 after transplanting (Feb. 18, 2009), week 12 after transplanting (Mar. 4, 2009), and week 14 after transplanting (Mar. 18, 2009). In Experiment 2, the severity of powdery mildew was assessed at week 8 after transplanting (Oct. 15, 2009), week 10 after transplanting (Oct. 29, 2009), and week 12 after transplanting (Nov. 12, 2009). A randomized complete block design was used with five replications in Experiment 1 and with eight replications in Experiment 2. The experimental unit was a single containerized plant. 'UFGE 7034' showed a moderate level of resistance to powdery mildew in both Experiment 1 and Experiment 2 (Table 1). 'UFGE 7034' remained to be more productive than 'Bimini' and 'Pensacola' when natural powdery mildew disease pressure existed (Table 1). No other disease resistance characterizations have been made.

TABLE 1

Powdery mildew severity ratings and inflorescence counts of 'UFGE 7034' and two commercial gerbera cultivars, 'Bimini' and 'Pensacola', grown under natural powdery mildew pressure in two experimental trials in Wimauma, FL. Experiment 1 (Winter 2008 through Spring 2009), Experiment 2 (Summer 2009 through Fall 2009)

| | PM Ratings[Z] | | | | Inflorescence |
|---|---|---|---|---|---|
| Cultivars | Week 8 | Week 10 | Week 12 | Week 14 | counts[Y] |
| Experiment 1 (Winter 2008 through Spring 2009) | | | | | |
| 'UFGE 7034' | 1.0 | 2.2 | 4.2 | 6.2 | 5.0 |
| 'Bimini' | 1.2 | 1.8 | 5.4 | 8.0 | 3.2 |
| 'Pensacola' | 1.0 | 2.0 | 4.8 | 8.6 | 3.0 |

TABLE 1-continued

Powdery mildew severity ratings and inflorescence counts of 'UFGE 7034' and two commercial gerbera cultivars, 'Bimini' and 'Pensacola', grown under natural powdery mildew pressure in two experimental trials in Wimauma, FL. Experiment 1 (Winter 2008 through Spring 2009), Experiment 2 (Summer 2009 through Fall 2009)

| | PM Ratings[Z] | | | | Inflorescence |
|---|---|---|---|---|---|
| Cultivars | Week 8 | Week 10 | Week 12 | Week 14 | counts[Y] |
| Experiment 2 (Summer 2009 through Fall 2009) | | | | | |
| 'UFGE 7034' | 1.0 | 3.1 | 5.5 | | 5.1 |
| 'Bimini' | 2.6 | 8.6 | 9.4 | | 2.6 |
| 'Pensacola' | 1.8 | 7.5 | 9.8 | | 1.1 |

[Z]Powdery mildew severity was rated on a scale of 1 to 10 as described by Hausbeck et al. (2002): 1 = no disease, 2 = trace to 10%, 3 = 10% to 20%, 4 = 20 to 30%, 5 = 30% to 40%, 6 = 40% to 50%, 7 = 50% to 60%, 8 = 60% to 70%, 9 = 70% to 80%, and 10 = 80% to 100% of leaf surface covered with powdery mildew.

[Y]Total number of inflorescences produced per plant over nine weeks from Jan. 20, 2009 to Mar. 17, 2009 in Experiment 1 or from Sep. 25, 2009 to Nov. 20, 2009 in Experiment 2, both in a screen house in Wimauma, FL.

COMPARISON WITH PARENTAL AND KNOWN CULTIVARS

'UFGE 7034' differs from the female parent 'UFGE 5006' (unpatented) by having full-double inflorescences in orange-red under growing conditions in Wimauma, Fla. 'UFGE 7034' differs from the male parent 'Sunburst Yellow' (unpatented) by having intermediate peduncles, full-double inflorescences, and a moderate level of powdery mildew resistance under growing conditions in Wimauma, Fla. In contrast, the female parent 'UFGE 5006' has light orange inflorescences, and the male parent 'Sunburst Yellow' has short peduncles, single inflorescences, and susceptibility to powdery mildew.

'UFGE 7034' can be compared to *Gerbera hybrida* 'UFGE 7032', disclosed in the co-pending application (Ser. No. 13/068,286). 'UFGE 7034' differs from 'UFGE 7032' in the following characteristics:

1. 'UFGE 7034' has full-double inflorescences while 'UFGE 7032' has semi-double inflorescences;
2. Inflorescences of 'UFGE 7034' are orange-red while those of 'UFGE 7032' are bright yellow;
3. 'UFGE 7034' has a more open, wider canopy while 'UFGE 7032' has a more compact canopy.
4. 'UFGE 7034' produces more inflorescences per plant than 'UFGE 7032'.

Comparisons were made with the commercial *gerbera* variety 'Bimini' (unpatented) and the commercial *gerbera* variety 'Pensacola' (unpatented). Two experiments were conducted in a greenhouse at Wimauma, Fla. under standard greenhouse management practices to evaluate the plant performance (days to flower, inflorescence quality, inflorescence count, and plant quality) of 'UFGE 7034' for container plant production in comparison to 'Bimini' and 'Pensacola'. In the first of the two plant performance experiments (Experiment 3), tissue culture liners were transplanted on Dec. 9, 2008 into 2.7-L containers filled with commercial potting mix amended with controlled release fertilizer at the rate of 5.28 $kg \cdot m^{-3}$ and trace element fertilizer at the rate of 1.05 $kg \cdot m^{-3}$. Potted plants were grown on metal benches in a glass house and spaced 46 cm×46 cm apart. Temperatures inside the greenhouse ranged from 18° C. to 33° C. Two hours of additional photoperiodic lighting were provided between Dec. 9, 2008 and Mar. 17, 2009. Fungicides and insecticides were applied as needed to control powdery mildew and western flower thrips. Inflorescence quality was rated on a 1 to 5 scale: 1=very poor, 3=fair, some blemishes, but acceptable, and 5=excellent, bright, uniform, and no blemishes. Inflorescence counts were recorded weekly from Jan. 20, 2009 through Mar. 17, 2009. Plant quality was rated three times, on Jan. 20, 2009, Feb. 3, 2009, and Feb. 17, 2009, using a 1 to 5 scale: 1=few leaves or long petioles, container surface visible, very poor and unacceptable as flowering pot plants, 3=fair and marketable, and 5=excellent, full, symmetrical, attractive plants.

In the second of the two plant performance experiments (Experiment 4), tissue culture liners were transplanted on Aug. 13, 2009 into 2.7-L plastic containers filled with commercial potting mix amended with controlled release fertilizer at the rate of 5.28 $kg \cdot m^{-3}$ and trace element fertilizer at the rate of 1.05 $kg \cdot m^{-3}$. Plants were grown on metal benches in a greenhouse with a spacing of 46 cm×46 cm. The greenhouse was covered with aluminum shading cloth with approximately 30% light exclusion. Greenhouse temperatures ranged from 21° C. to 35° C. Two hours of additional photoperiodic lighting was provided beginning Sep. 15, 2009. Fungicides and insecticides were applied as needed to control powdery mildew and western flower thrips. Inflorescence quality and plant quality were rated as above for Experiment 3, but on Sep. 25, 2009, Oct. 15, 2009, and Nov. 5, 2009. The number of inflorescences produced per plant was recorded weekly from Sep. 25, 2009 through Nov. 20, 2009.

The experiment design for the plant performance experiments was a randomized complete block design with five replications in Experiment 3 and eight replications in Experiment 4. The experimental unit was a single containerized plant.

'UFGE 7034' came into flowering 24 to 29 days earlier than 'Bimini' and 'Pensacola' in Experiment 3 and 9 to 15 days earlier than 'Bimini' and 'Pensacola' in Experiment 4 (Table 2). Inflorescence quality ratings of 'UFGE 7034' were 4.9, similar to that of 'Bimini' (5.0 to 4.8), and higher than that of 'Pensacola' (4.1 to 4.3) (Table 2). In both Experiment 3 and Experiment 4, 'UFGE 7034' produced more inflorescences (340% to 729% more than 'Bimini' and 220% to 484% more than 'Pensacola') (Table 2). The plant quality ratings of 'UFGE 7034' were 4.5 to 4.6, higher than that of the controls (Table 2).

TABLE 2

Plant performance of 'UFGE 7034' and two commercial cultivars, 'Bimini' and 'Pensacola' grown in Experiment 3 (Winter 2008 through Spring 2009) and Experiment 4 (Summer 2009 through Fall 2009) in Wimauma, Florida.

| Cultivars | Days to 1st open inflorescences (no.) | Inflorescence quality[Z] | Inflorescence counts[Z] (no.) | Plant quality[Y] |
|---|---|---|---|---|
| Experiment 3 (Dec. 9, 2008 to Mar. 17, 2009) | | | | |
| 'UFGE 7034' | 39.8 | 4.9 | 10.2 | 4.5 |
| 'Bimini' | 64.0 | 5.0 | 3.0 | 3.1 |
| 'Pensacola' | 68.8 | 4.1 | 1.4 | 3.3 |
| Experiment 4 (Aug. 13, 2009 to Nov. 20, 2009) | | | | |
| 'UFGE 7034' | 41.3 | 4.9 | 12.1 | 4.6 |
| 'Bimini' | 50.1 | 4.8 | 5.5 | 3.2 |
| 'Pensacola' | 55.8 | 4.3 | 2.5 | 3.3 |

[Z]Inflorescence count data were collected over nine weeks from Jan. 20, 2009 to Mar. 17, 2009 in Experiment 3 and another nine weeks from Sep. 25, 2009 to Nov. 20, 2009 in Experiment 4. Each value represents the mean of five (Experiment 3) or eight (Experiment 4) replicates.

[Y]The plant quality rating value in Experiment 3 was the mean of five replicates over three times (Jan. 20, Feb. 3, and Feb. 17, 2009), and the plant quality rating value in Experiment 4 was the mean of eight replicates over three times (Sep. 25, Oct. 15, and Nov. 5, 2009).

OTHER CHARACTERISTICS

'UFGE 7034' is noted for its very sturdy inflorescence. The edges of its outer ray florets tend to curl slightly upward, making the yellow-orange underside color (RHS 23C) easily visible and giving the appearance of a yellow petal edge.

Literature Cited

Hausbeck, M. K., W. R. Quackenbush, and S. D. Linderman. 2002. Evaluation of cultivars of African daisy for resistance to powdery mildew, 2002. B&C Tests 18:O0004.

We claim:

1. A new and distinct cultivar of *Gerbera* plant named 'UFGE 7034', as illustrated and described herein.

* * * * *